(12) United States Patent
Martino et al.

(10) Patent No.: US 10,420,525 B2
(45) Date of Patent: Sep. 24, 2019

(54) METHOD AND APPARATUS FOR ALIGNING OF CEPHALOMETRIC IMAGING DEVICE COLLIMATOR

(71) Applicant: TROPHY, Croissy-Beaubourg (FR)

(72) Inventors: Olivier Martino, Marne la Vallee (FR); Yann Lecuyer, Paris (FR); Chloe Abdoul-Carime-Comparetti, Vincennes (FR)

(73) Assignee: TROPHY, Croissy-Beaubourg (FR)

( * ) Notice: Subject to any disclaimer, the term of this patent is extended or adjusted under 35 U.S.C. 154(b) by 114 days.

(21) Appl. No.: 15/546,402

(22) PCT Filed: Apr. 3, 2015

(86) PCT No.: PCT/IB2015/001225
§ 371 (c)(1),
(2) Date: Jul. 26, 2017

(87) PCT Pub. No.: WO2016/156911
PCT Pub. Date: Oct. 6, 2016

(65) Prior Publication Data
US 2018/0021007 A1    Jan. 25, 2018

(51) Int. Cl.
*A61B 6/00*     (2006.01)
*A61B 6/14*     (2006.01)
(Continued)

(52) U.S. Cl.
CPC .................. *A61B 6/58* (2013.01); *A61B 6/04* (2013.01); *A61B 6/06* (2013.01); *A61B 6/14* (2013.01); *A61B 6/501* (2013.01)

(58) Field of Classification Search
CPC ................ A61B 6/58; A61B 6/04; A61B 6/06
See application file for complete search history.

(56) References Cited

U.S. PATENT DOCUMENTS

2002/0106053 A1   8/2002   Suuronen
2015/0305696 A1*   10/2015   Yamakawa ............... A61B 6/14
                                                                                              378/19

FOREIGN PATENT DOCUMENTS

EP        3 277 184 A1    2/2018
JP        H10-211194 A    8/1998
(Continued)

OTHER PUBLICATIONS

Promax Pan et al, "Planmeca ProMax Pan/Ceph Calibration Manual", Jan. 26, 2009, retrieved from the Internet: URL:ftp://ftp.eaglesoft.net/Canada/TST/Patterson%20Toronto/Planmeca/Quick%20Manuals/Quick%20ProMax%20Cal.pdf, pp. 1-100.
(Continued)

*Primary Examiner* — Hugh Maupin

(57) ABSTRACT

An extra-oral imaging apparatus is intended to obtain a cephalometric image of a portion of a head of a patient. Exemplary apparatus embodiments of cephalometric functionality of such extra-oral imaging apparatus can include a cephalometric support mounted to a base of the imaging system that is configured to position a cephalometric sensor about a cephalometric imaging area so that x-rays impinge the cephalometric sensor after radiating the cephalometric imaging area. A cephalometric collimator can be mounted to a patient positioning unit to provide secondary collimation of the x-ray beam for the cephalometric sensor. Exemplary apparatus and/or method embodiments of the application relates to providing a measurable indication of alignment between a cephalometric collimator and cephalometric sensor or the extra-oral imaging apparatus, which can provide a repeatable and/or accurate alignment between a cephalometric collimator and cephalometric sensor.

10 Claims, 15 Drawing Sheets

(51) Int. Cl.
*A61B 6/04* (2006.01)
*A61B 6/06* (2006.01)

(56) References Cited

FOREIGN PATENT DOCUMENTS

| | | |
|---|---|---|
| JP | 2002-238889 A | 8/2002 |
| JP | 2014-151198 A | 8/2014 |
| JP | 2014-523331 A | 9/2014 |
| JP | 2018-509950 A | 4/2018 |
| KR | 10-2017-0137037 A | 12/2017 |
| WO | 2013/014488 A1 | 1/2013 |
| WO | 2014/033614 A1 | 3/2014 |
| WO | 2014/171833 | 10/2014 |
| WO | 2016/156911 A1 | 10/2016 |

OTHER PUBLICATIONS

International Search Report, dated Jan. 1, 2016, International Application No. PCT/IB2015/001225, 3 pages.
Notification of Reasons for Refusal for Japanese Patent Application Serial No. 2017-539001 date Oct. 30, 2018, 4 pages (including English Translation).
International Preliminary Report on Patentability for International Patent Application Serial No. PCT/IB2015/001225 dated Oct. 12, 2017, 7 pages.

* cited by examiner

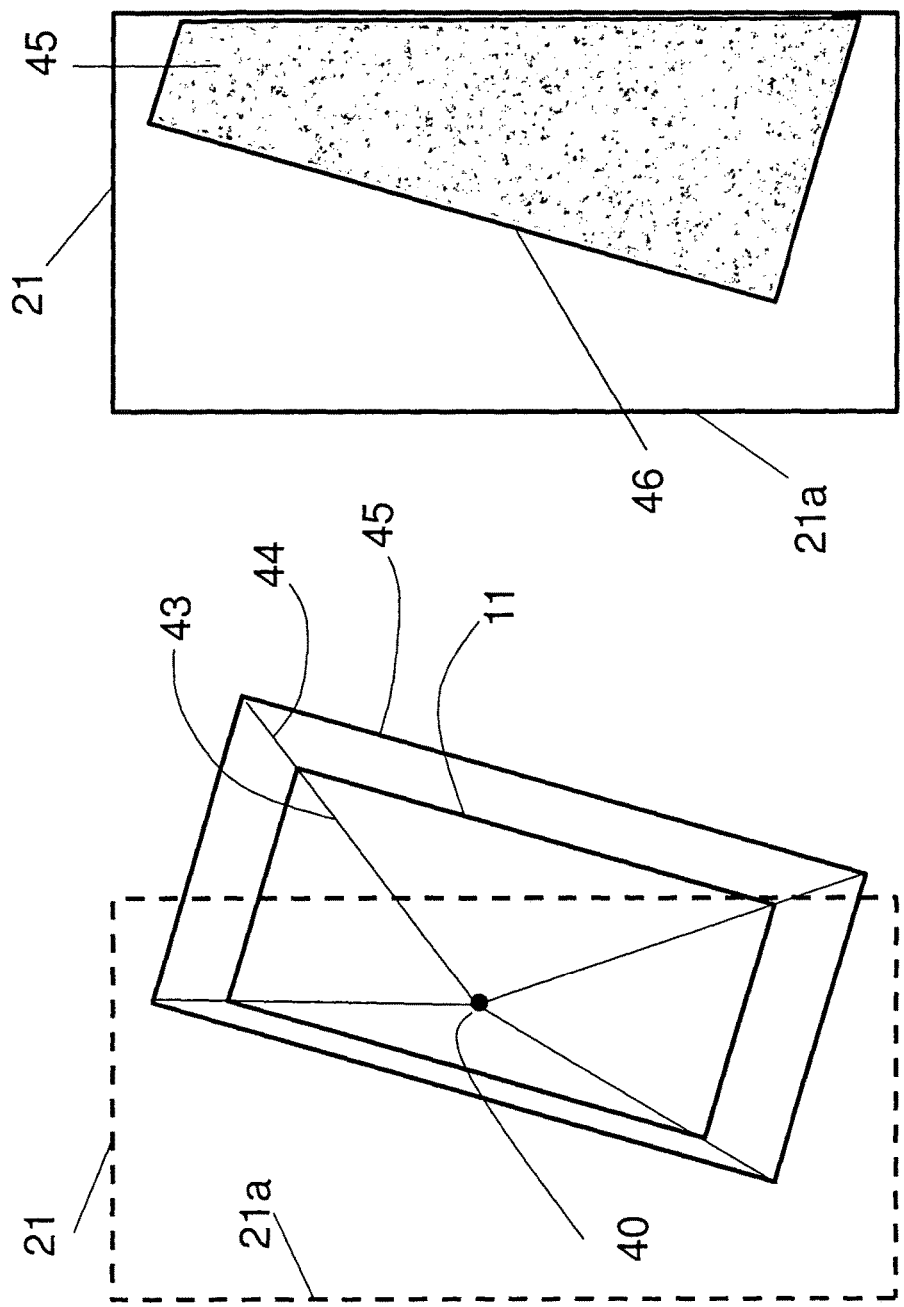

METHOD AND APPARATUS FOR ALIGNING OF CEPHALOMETRIC IMAGING DEVICE COLLIMATOR

CROSS REFERENCE TO RELATED APPLICATIONS

This application claims the benefit of and is a U.S. National Phase filing of PCT Application PCT/IB15/01225 filed Apr. 3, 2015, entitled "METHOD AND APPARATUS FOR ALIGNING OF CEPHALOMETRIC IMAGING DEVICE COLLIMATOR", in the name of Martino et al., which is incorporated herein by reference in its entirety.

FIELD OF THE INVENTION

The invention relates generally to the field of dental x-ray imaging, and more particularly, to a cephalometric x-ray imaging functionality for dental applications. Further, the invention relates to a cephalometric dental imaging apparatus and/or methods.

BACKGROUND

Cephalometric imaging (or transillumination imaging) is regularly used by dental practitioners, for example, in orthodontic applications. For cephalometric imaging techniques, an image of the x-ray radiated skull of the patient is projected on an x-ray sensitive surface located away from the x-ray source using a cephalometric arm. In most of the cases, the sensor is positioned at the extremity of a long cephalometric arm and is positioned at a distance about 1.8 meters away from the x-ray source. The necessity to have the sensor positioned far away from the x-ray source originates from the necessity to have an approximately equal magnitude factor for every part of the patient's skull. The imaging process may consist in one single shot of the patient's skull with the x-ray beam impinging a full (e.g., square) sensor after radiating the patient. One advantage of single shot image acquisition is that it can be short in time, less than one second. The single shot image can reduce effects from any motion of the patient. One drawback of single shot image acquisition is that the large sensor is very expensive. As an alternative to decrease the size of the sensor, a linear elongated sensor can be used in association with a linearly elongated (e.g., vertical) slit-shaped collimator that aims at shaping the x-ray beam before the x-ray beam radiates the patient. The patient is positioned between the elongated collimator and the elongated sensor. A linear scan can be performed by horizontally translating a vertically elongated sensor and a vertically elongated collimator and changing the direction of the x-ray beam accordingly through the use of a primary collimator positioned in front of the X-ray source. The images collected during the scan are merged together to form a projection of the patient's skull. In the cephalometric or skull imaging technique, the patient can be positioned facing the x-ray beam or in a profile position.

Most current manufacturers use a small elongated sensor that can slide to carry out a scan of the whole patient's head. In scanning image acquisition, both a primary collimator, which may be a variable collimator, in front of an x-ray source and a second collimator (e.g., cephalometric collimator), which may be a variable collimator, positioned before the patient's head are slit-shaped. The secondary collimator and the x-ray sensor simultaneously slide during the scan in such a way that the center of the apertures of the variable primary collimator, the center of the aperture of the secondary collimator and the center of the x-ray sensor are all three aligned at any time of the scan. Such an alignment is known from the related art. Again, a plurality of images are collected by the elongated x-ray sensor, stored and stitched together to create a whole skull image.

The direction of the secondary collimator's slit and the direction of the elongated active surface area of the sensor may not be perfectly parallel (e.g., misaligned or the secondary collimator or collimator aperture/slit can be tilted relative to the active area of the x-ray sensor). Misalignment of the secondary collimator and the x-ray sensor can lead to truncated images and/or some x-rays that radiate the patient are then not collected by the x-ray sensor, which can lead to unnecessary exposure of the patient. Conventional apparatus and/or methods of alignment are long and cumbersome and necessitate iterative attempts to align both directions and include successive corrective positioning of the collimator's tilt followed by imaging tests. Such an alignment is complicated by the fact that the cephalometric imaging unit is located at a large distance away from the source of x-ray beam.

It can be appreciated that there is still a need for installation apparatus and/or methods that can provide a cheaper, rapid, and/or accurate assessment of a correctness of an installation/adjustment/alignment of a cephalometric module (e.g., dental cephalometric imaging device) or alignment (e.g., vertical) of a slit of the secondary collimator and the elongated active area of the x-ray sensor of a cephalometric module.

SUMMARY

An aspect of this application is to advance the art of medical digital radiography, particularly for dental cephalometric applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to providing a measurable indication of alignment between a cephalometric collimator and cephalometric imaging sensor.

Another advantage offered by apparatus and/or method embodiments of the application relates to providing a repeatable and/or accurate indication of alignment between a cephalometric collimator and cephalometric imaging sensor.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the disclosure, there is provided a method for aligning a cephalometric imaging unit to an extra-oral imaging system that can include

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting x-ray system components, for example, are not shown in the drawings in order to simplify description.

FIG. 3 is a diagram that shows a longitudinal view representing, an x-ray source, a secondary collimator, a cephalometric sensor and a projection of the twice collimated beam from the x-ray source on the geometric plane of the cephalometric sensor.

FIG. 4 is a diagram that shows represents the area of the active surface of the sensor that is impinged by the x-ray beam for an initial position of the secondary collimator relative to the x-ray sensor.

DESCRIPTION OF EXEMPLARY EMBODIMENTS

Figure 1:
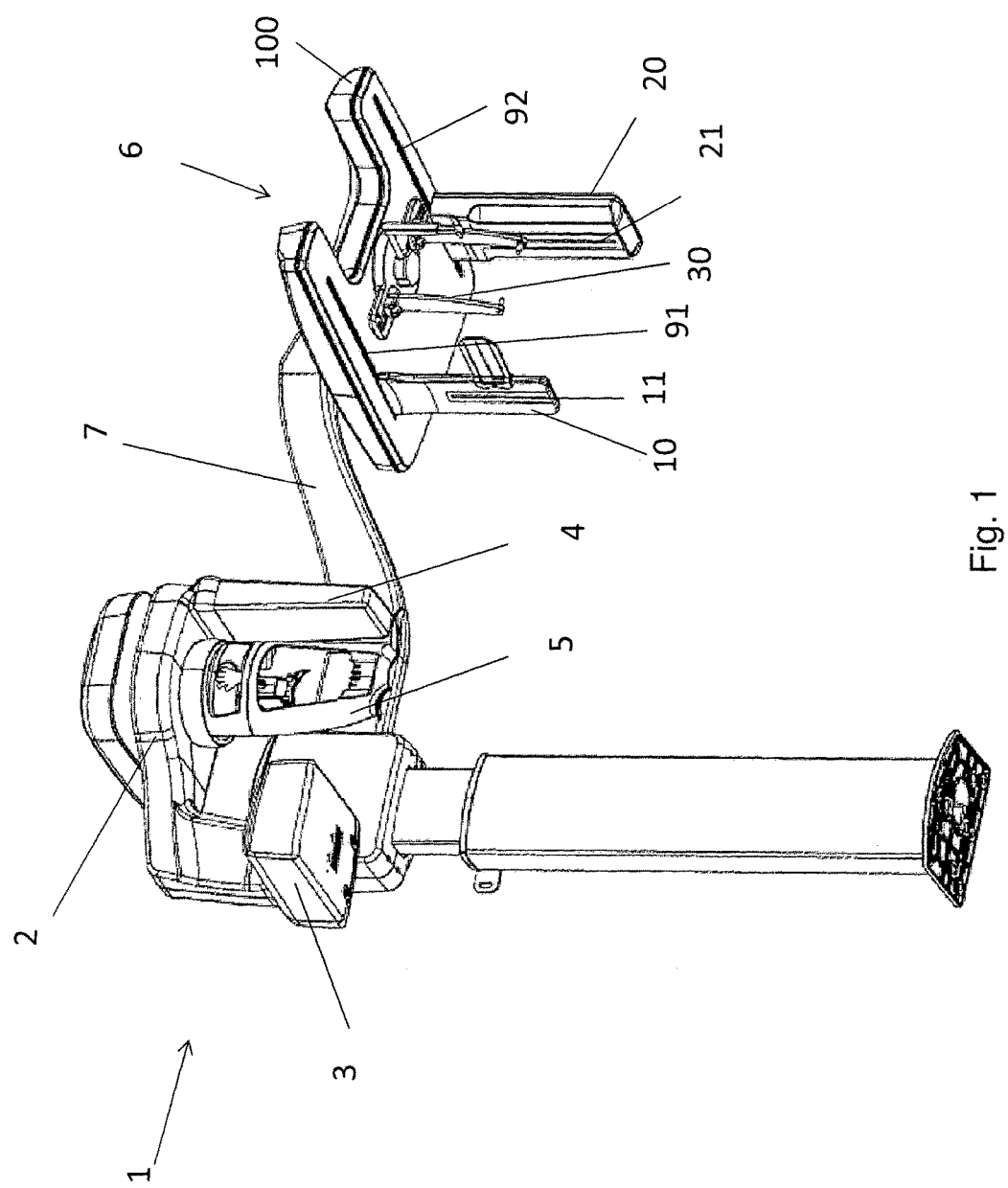
FIG. 1 is a diagram that shows an extra oral imaging device including a cephalometric imaging module.

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Apparatus and/or method embodiments according to the application aim at facilitating an installation process by giving the technician a highly precise rapid assessment of the correctness of the adjustment of the cephalometric collimator.

FIG. 1 is a diagram that shows an extra oral imaging device including a cephalometric imaging module. As shown in FIG. 1, an extra oral x-ray imaging device 1 for use with embodiments of the application can include a gantry 2 supporting an x-ray source 3 comprising a focal spot 40, embodied with a variable primary collimator 42 and a CT and/or panoramic sensor 4 facing the x-ray source 3 with a patient's positioner 5 in-between. The x-ray source 3 and sensor 4 can be near opposite ends of gantry 2. A cephalometric imaging unit 6 is mounted on (e.g., positioned at the end of) a cephalometric arm 7. Due to the long distance between the x-ray source 3 and a cephalometric sensor 20 (typically 1.8 m), a primary collimator 42 in front of the x-ray source 3 cannot collimate the x-ray beam 43 precisely enough. A secondary collimator 10 with an aperture 11 (e.g., elongated or slit-shaped) is held on a cephalometric platform 100 and can slide along a first rail 91. Then, a beam 43 originating from the x-ray source 3 and shaped by the primary collimator 42 can be shaped a second time into an x-ray beam 44 by the secondary collimator 10. A cephalometric sensor 20 with an elongated active area 21 is also held on the cephalometric platform 100 and can slide along a second rail 92. A patient holder 30 to fixedly hold the patient can be located between the secondary collimator 10 and the sensor 20.

Figure 2:
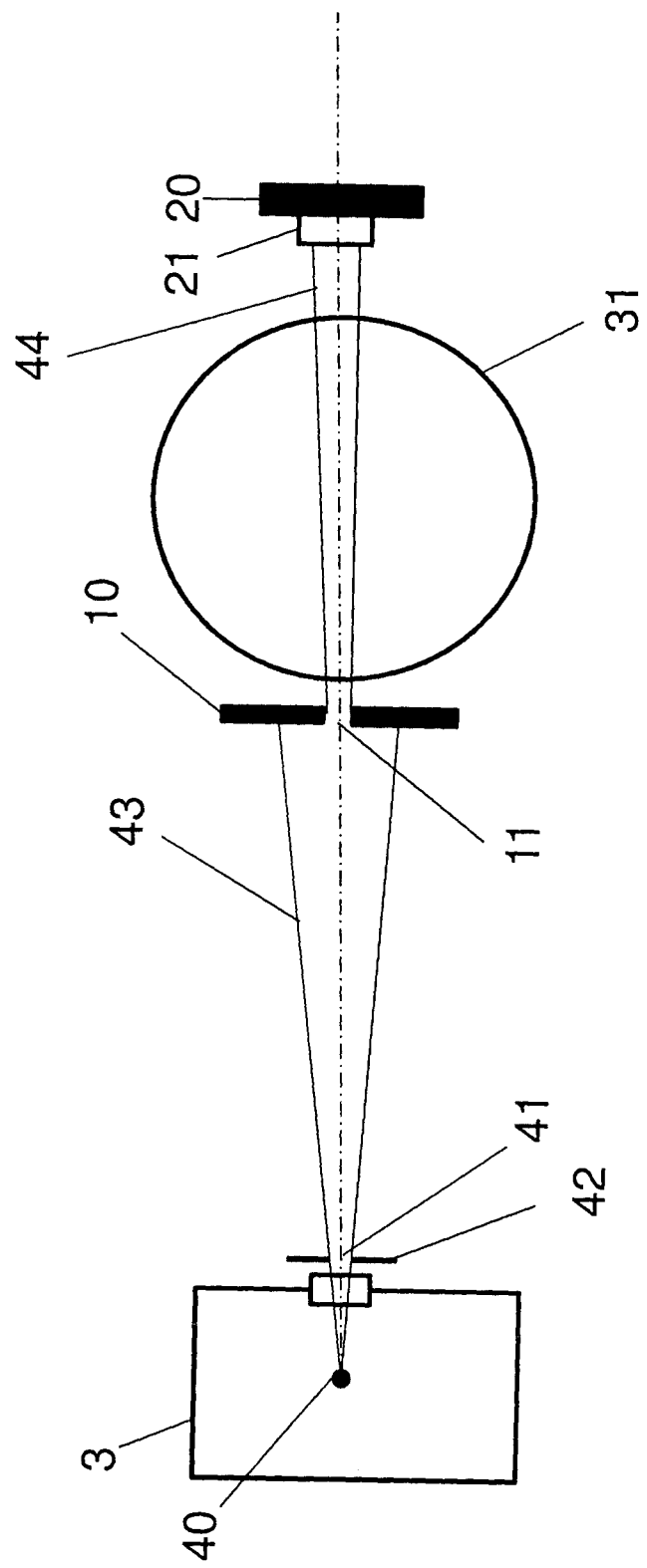
FIG. 2 is a diagram that shows a top view of an ensemble including an x-ray source with a first collimator, a second collimator and a cephalometric sensor.

FIG. 2 is a diagram that shows a top view of an ensemble including an x-ray source with a first collimator, a second collimator and a cephalometric sensor. As shown in FIGS. 1-2, the sliding movement of the collimator 10 and the sensor 20 can be controlled in such a way that a center of the aperture 41 of the primary collimator 42 of the x-ray source 3, the center of the aperture 11 of the secondary collimator 10 and the center of the active area 21 of the sensor 20 are aligned at any time of the scan of the patient head 31 extra oral x-ray imaging device 1.

FIG. 3 is a diagram that shows a longitudinal view representing an x-ray source, a secondary collimator, a cephalometric sensor and a projection of a twice collimated beam from the x-ray source on the geometric plane of the cephalometric sensor. As shown in FIG. 3, the direction of the slit 11 of the secondary collimator 10 is not parallel to the direction of the elongated active area 21 of the sensor 20. The geometric plane of the cephalometric sensor is shown from the direction of the x-ray beam 43 in FIG. 3. The beam 43 originating from the focal spot 40 of the source 3 is shaped into the beam 44 by the slit 11 of the collimator 10. The beam 44 then projects toward the geometrical plane of the sensor as an area 45 that may only partially coincide with the active area 21 of the sensor. FIG. 4 is a diagram that is a representation of the image obtained from the misalignment of FIG. 3. It is noticed especially that the edge 46 of the surface 45 of the sensor is not parallel to the edge 21a of the active area of the sensor. FIG. 4 can represent the area of the active surface 21 of the sensor 20 that is impinged by the x-ray beam 44 for an initial position of the secondary collimator 10 relative to the x-ray source/sensor. Then, the tilt of the direction of the slit 11 of the collimator 10 relative to the direction of the active area 21 of the sensor 20 has to be corrected by method and/or apparatus embodiments according to the invention.

Further, it is also observed in FIG. 3 (and FIG. 4) that a center of the slit 11 of the collimator 10 is not centered on the line joining the focal spot 40 of the x-ray source 3 and a center of the active area 21 of the sensor 20. Thus, in certain exemplary embodiments in a second step, it can be necessary to correct this offset (e.g., of the aperture 11 center position and active area 21 center position) by centering the collimator 10 relative to the sensor 20.

Figure 5:
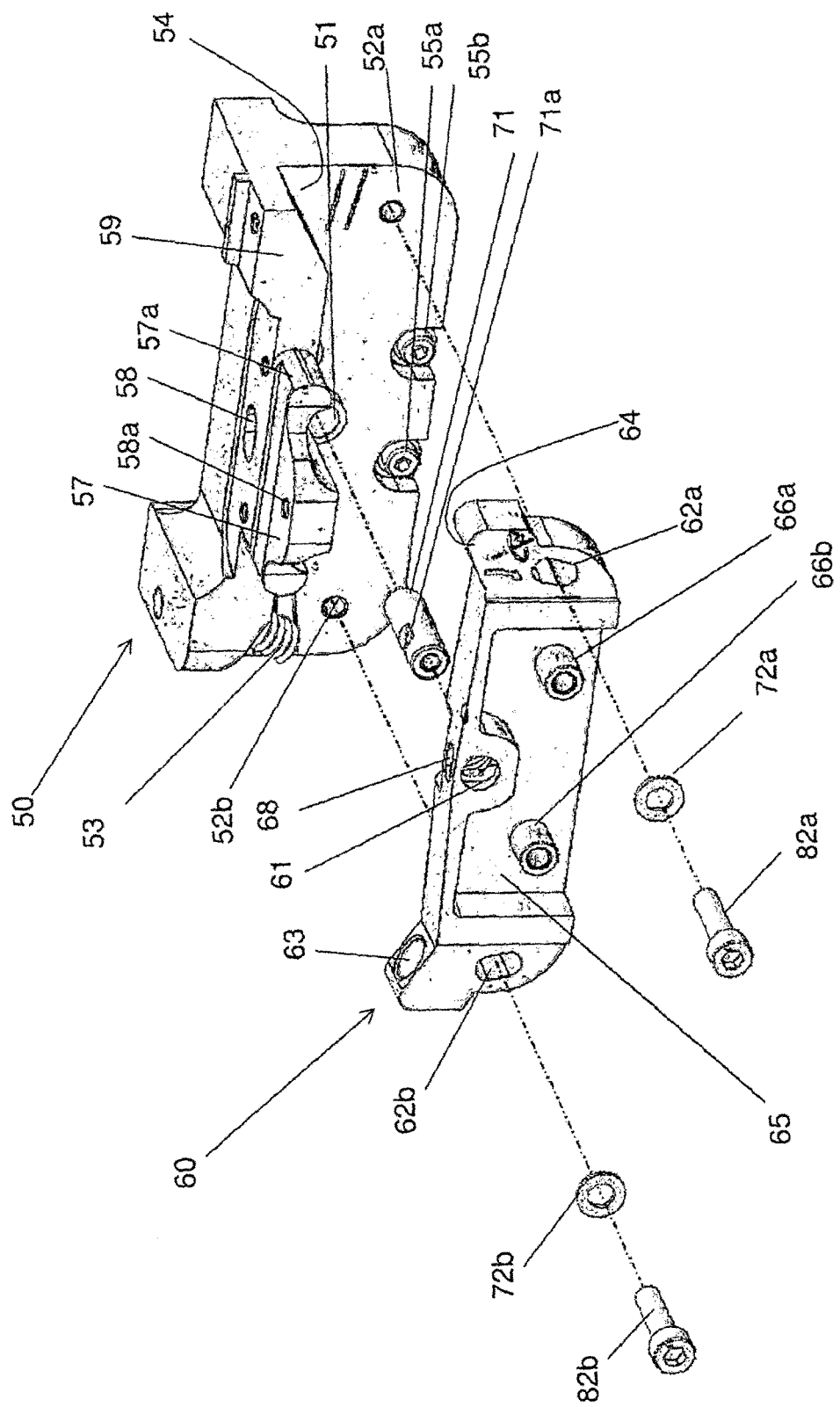
FIG. 5 is a diagram that shows an exploded view of the ensemble comprising an exemplary carriage and an exemplary platen with fixing means according to embodiments of the application.
Figure 6:
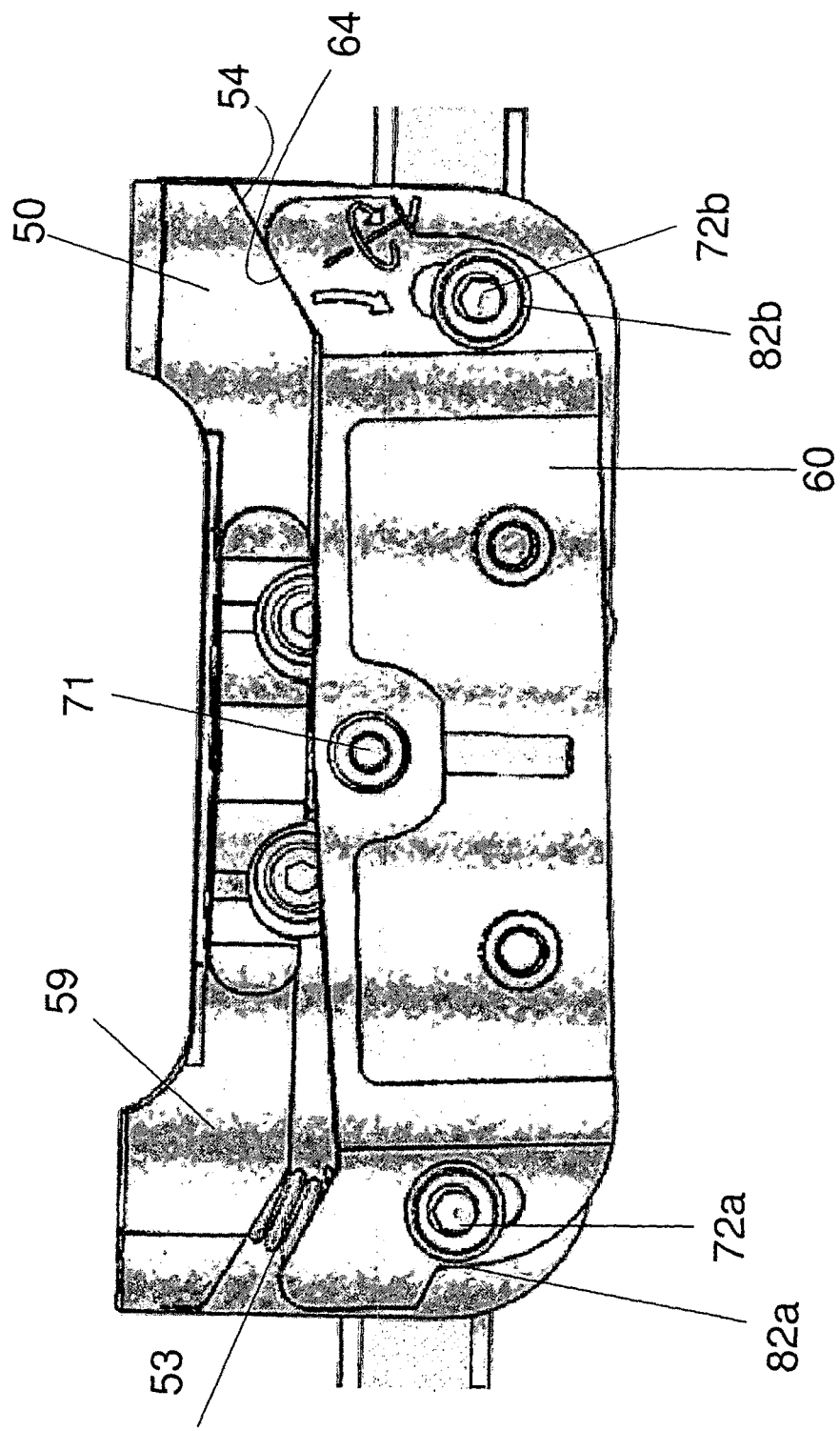
FIGS. 6 and 7 are diagrams that show two different representative positions of a platen relative to a carriage according to embodiments of the application.

For the purpose of correcting the mis-alignment tilt of the collimator 10 to imaging device 1, in embodiments of the application the collimator 10 can be movably fixed or rotatably fixed on an ensemble sliding along the first rail 91. FIG. 5 is a diagram that shows an exploded view of an ensemble including an exemplary carriage and an exemplary platen with fixing means according to embodiments of the application. A platen 60 can be positioned relative to a carriage 50 by a shaft 71 passing through a hole 61 of the platen 60 and a hole 51 of the carriage 50. As described herein, in one exemplary embodiment the shaft 71 can act as a rotation axis for a small angle rotation movement of the platen 60 relative to the carriage 50. The shaft 71 is provided with a bore 71a about its mid portion. A first protrusion 59 extends from the lateral face of the carriage 50. An urging force can rotate the platen 60 relative to the carriage 50. In one embodiment, a spring 53 is attached to a lower face of first protrusion 59 and is housed in a bore 63 of the platen 60 when the platen 60 is positioned against the carriage 50. The force exerted by the spring 53 against the bottom of the bore 63 leads to a rotation of the platen 60 about the axis 71 relative to the carriage 50 so that an upper face 64 of the platen 60 contacts a lower face 54 of the protrusion 59 of the carriage 50. The platen 60 is then tilted relative to the carriage 50, as shown in FIG. 6.

Figure 7:
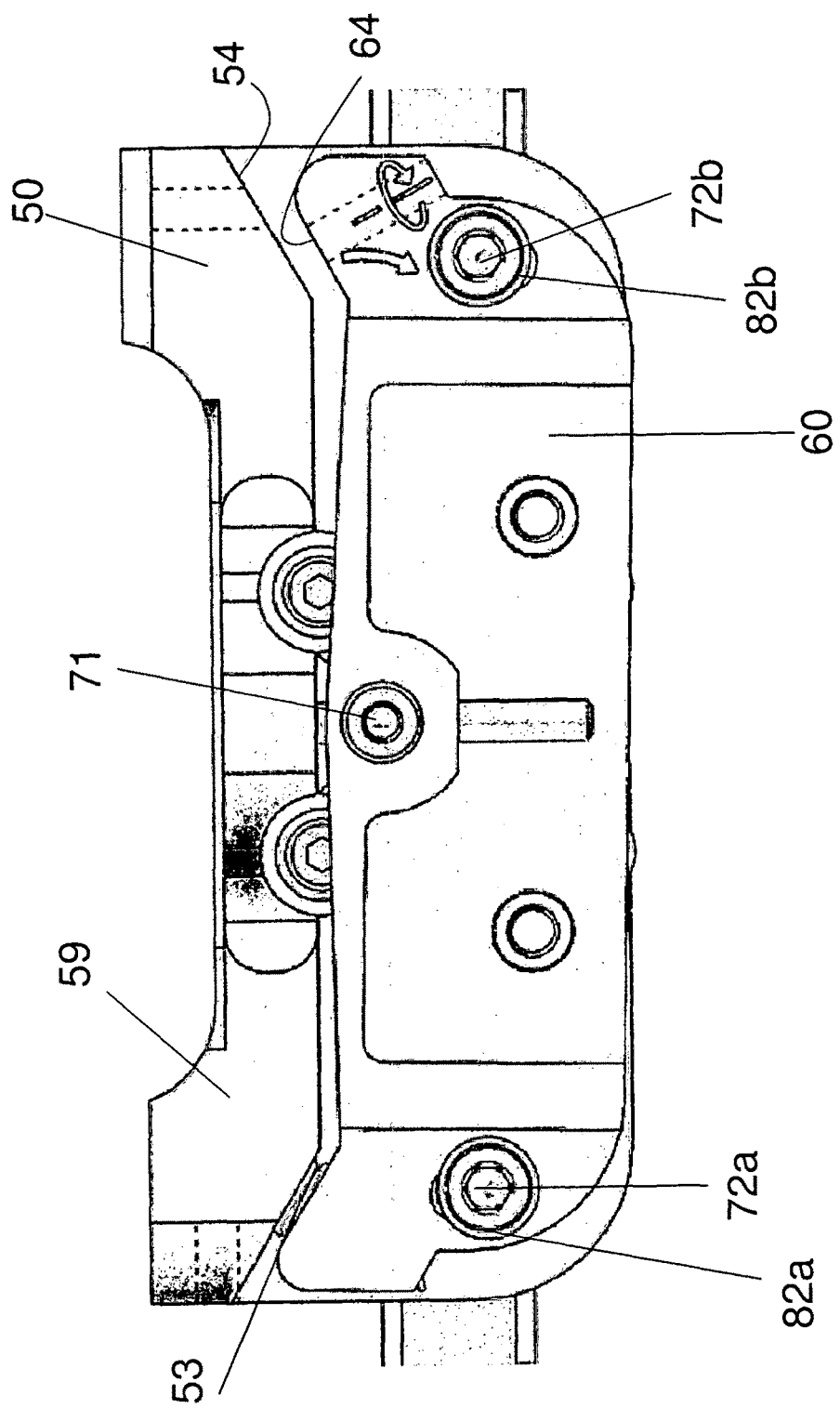

For certain exemplary embodiments, the platen 60 can be fixedly positioned to the carriage 50 by various conventional devices in an intermediate position or where the upper face 64 of the platen 60 does not contact the lower face 54 of the carriage 50. In one exemplary embodiment, a fixing unit or a fixing device such as fixing means 72a, 72b, 82a, 82b can be provided to fix the platen 60 relative to the carriage 50 at a position in which the surfaces 54 and 64 are not abutted (e.g., against the force of the spring 53). Two screws 82a and 82b can penetrate through two oblong holes 62a and 62b milled on the carriage 60 and through two threaded bores 52a and 52b of the carriage 50. Two washers 72a and 72b can be located between the screws 82a and 82b and the face of the platen 60. As long as the screws 82a and 82b are not tightly screwed into the bores 52a and 52b, the platen 60 can freely rotate relative to the carriage 50. For example, the largest dimension (e.g., length) of the oblong holes 62a and 62b is far larger than the diameter of the screws 82a and 82b that penetrate the oblong holes. Then, the oblong holes 62a and 62b of the platen 60 can be displaced relative to the screws 82a and 82b fixed in the threaded bores 52a and 52b of the carriage 50. On the contrary, when the screws 82a and 82b are tightly screwed in the threaded bores 52a and 52b, the washers 72a and 72b are pressed against the part of the face 65 of the platen 60 surrounding the oblong holes 62a and 62b. For example, the washers 72a and 72b can be chosen such that their diameter is larger than the width of the oblong holes 62a and 62b. The carriage 50 and the platen 60 are then in a fixed relationship. In examples of the fixed relationship case, the relative positioning between the carriage 50 and the platen 60 may be different from the position imposed by the action of the spring 53 described above (see FIG. 6) and the surface 64 of the platen 60 and the surface 54 of the carriage 50 may not be in contact as shown in FIG. 7. In one embodiment, any other relative position is achievable when the friction strength between the screws 82a and 82b and the face 65 of the platen 60 counterbalances the action of the spring 53.

Figure 8:
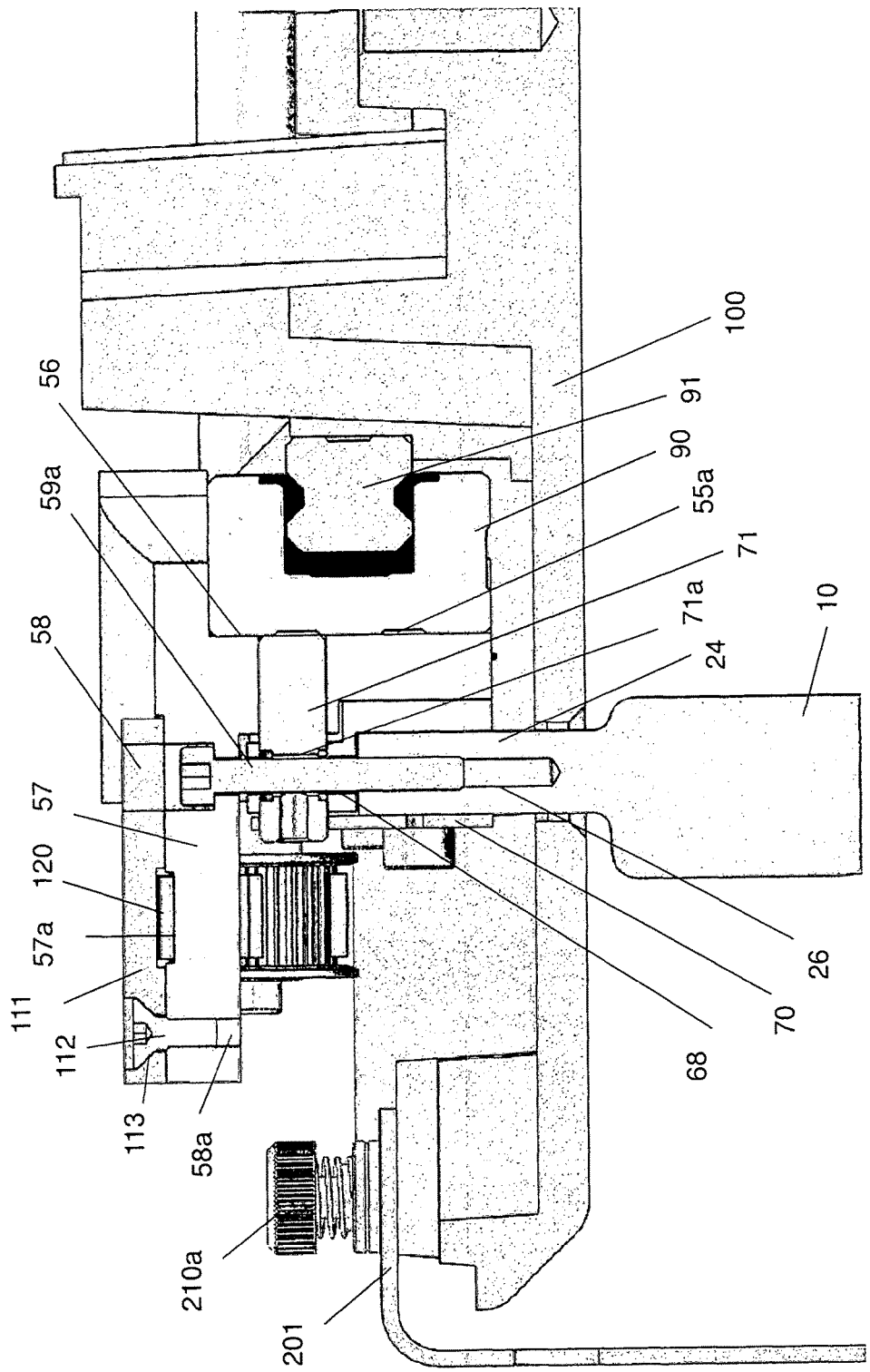
FIG. 8 is a diagram that shows a cross section of an exemplary ensemble embodiment including a carriage and a platen that are secured to a belt and positioned on a guiding rail of a cephalometric platform, where the carriage and platen are holding a secondary collimator according to the application.
Figure 9:
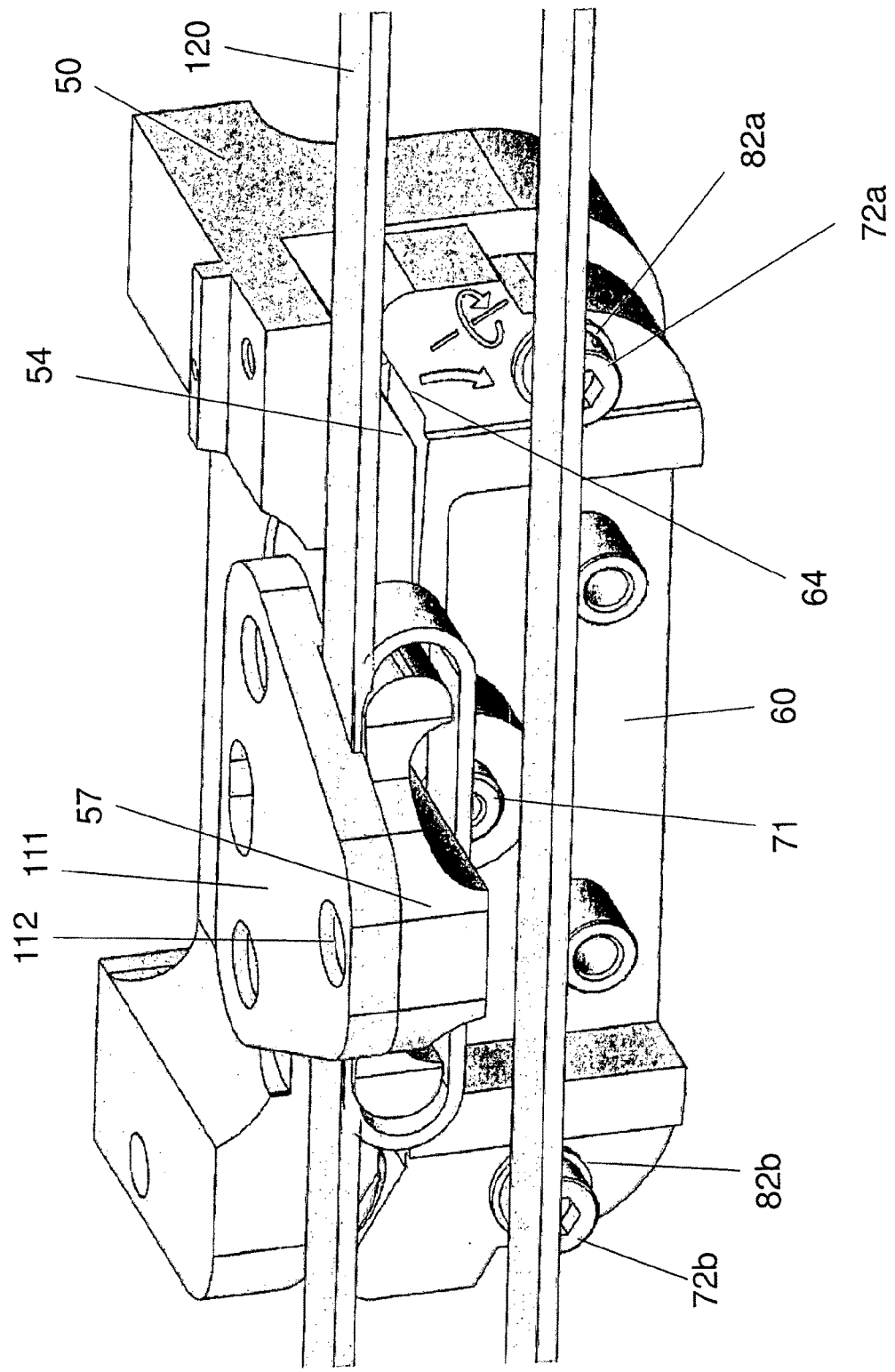
FIG. 9 is a diagram that shows an isometric view of the exemplary ensemble embodiment of FIG. 8 secured to the guiding rail according to the application.

FIG. 8 is a diagram that shows a cross section of an exemplary ensemble embodiment including a carriage and a platen that are secured to a belt and positioned on a guiding rail of a cephalometric platform, where the carriage and platen are holding a secondary collimator according to the application. FIG. 9 shows an isometric view of the exemplary ensemble embodiment of FIG. 8 secured to the guiding rail according to the application. The carriage 50 can include a second protrusion 57 that includes a groove 57a in which a belt 120 can be housed. A plate 111 can press the belt 120 against the protrusion 57 so that the belt cannot slide relative to the carriage 50. A screw 112 can penetrate through the hole 113 of the plate 111 and into the threaded bore 58a of the protrusion 57 of the carriage 50 to secure the contact between the belt 120 and the carriage 50.

A guide rail 90 is positioned in a recess 56 in the rear face of the carriage 50 and the carriage 50 can be secured to the guide rail by two screws 55a and 55b (see FIG. 5). The guide rail 90 slides along a rail 91 that elongates in a direction parallel to one side of the cephalometric platform 100 (see FIG. 10). A stepping motor 130 or the like can produce the displacement of the belt 120 via a displacement mechanism 131. As the belt 120 is secured to the carriage 50, which is itself secured on the guide rail 90 that slides along the rail 91, the motor 130 can displace the carriage 50 along the rail 91.

Figure 11:
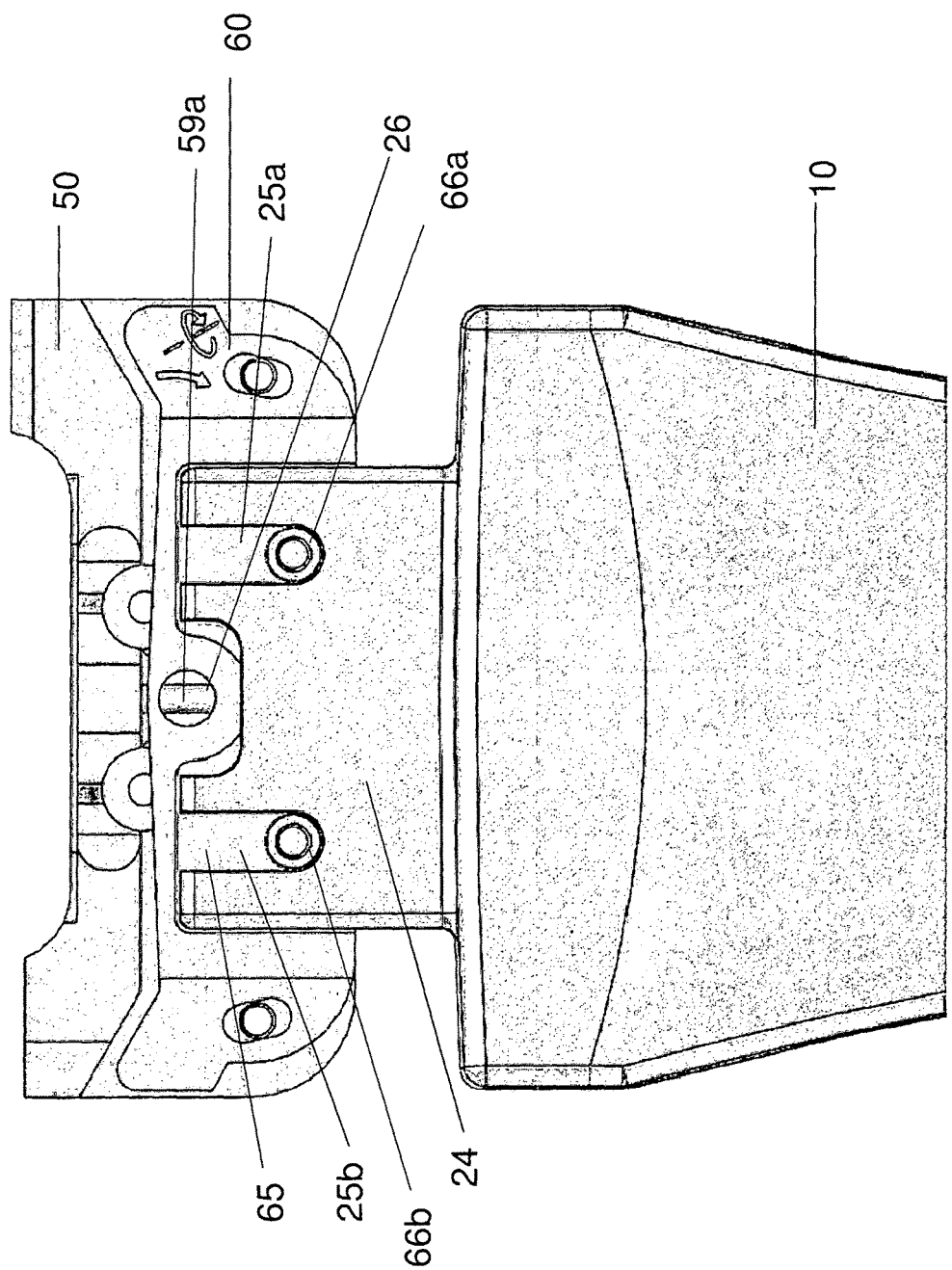
FIG. 11 is a diagram that shows a front view of an exemplary connection of a secondary collimator on the carriage and the platen according to embodiments of the application.

FIG. 11 is a diagram that shows a front view of an exemplary connection of a secondary collimator to a guide rail according to embodiments of the application. The collimator 10 can be fixed on an ensemble including the carriage 50 and the platen 60 by a long screw 59a that passes through the hole 58 of the carriage 50 (see FIG. 8), the hole 68 on the surface of the upper edge of the platen 60, the hole 71a that traverses the shaft 71 and finally a threaded bore 26 in the protrusion 24 of the cover of the collimator 10. Two notches 25a and 25b can be also provided on the protrusion 24 of the cover of the collimator 25 to engage the protrusions 66a and 66b on the surface 65 of the carriage 60 (see FIG. 11). A plate 70 can press the protrusion 24 of the cover of the collimator 10 against the face 65 of the platen 60. In this way, the collimator 10 is rigidly fixed to the platen 60 and consequently has the same position and/or direction as the platen 60 relative to the carriage 50.

Figure 10:
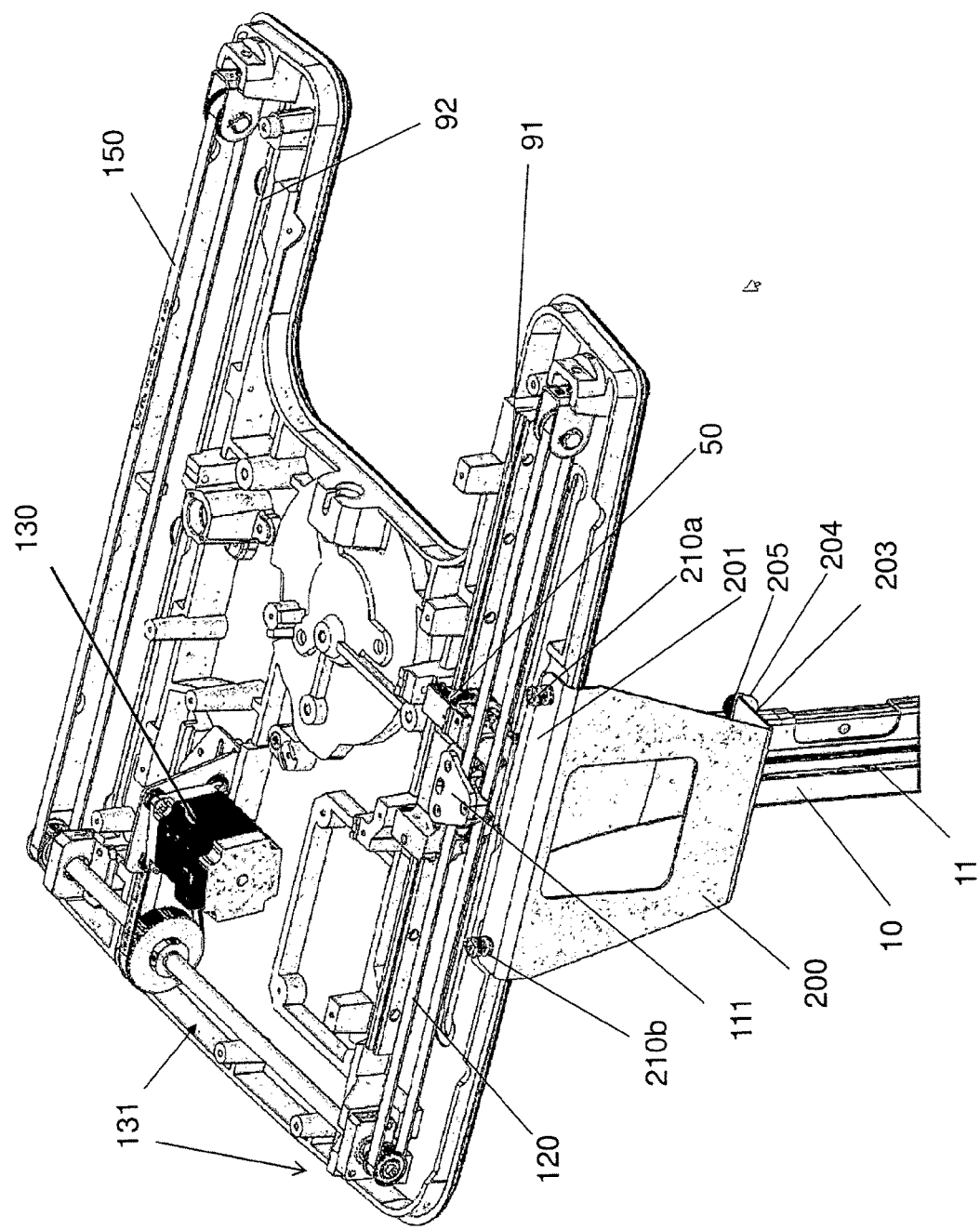
FIG. 10 is a diagram that shows an exemplary detachable tilting device embodiment attached to a cephalometric platform according to the application.

The sensor 20 (not shown) can be fixed on an exemplary mechanism secured to a second belt 150 (see FIG. 10). This exemplary mechanism can slide along the rail 92 by actuation of the belt 150 by the stepping motor 130. The exemplary mechanism can be conceived or formed in such a way that the sensor 20 is always vertical, that is to say orthogonal to the plane of the cephalometric platform 100.

Figure 12:
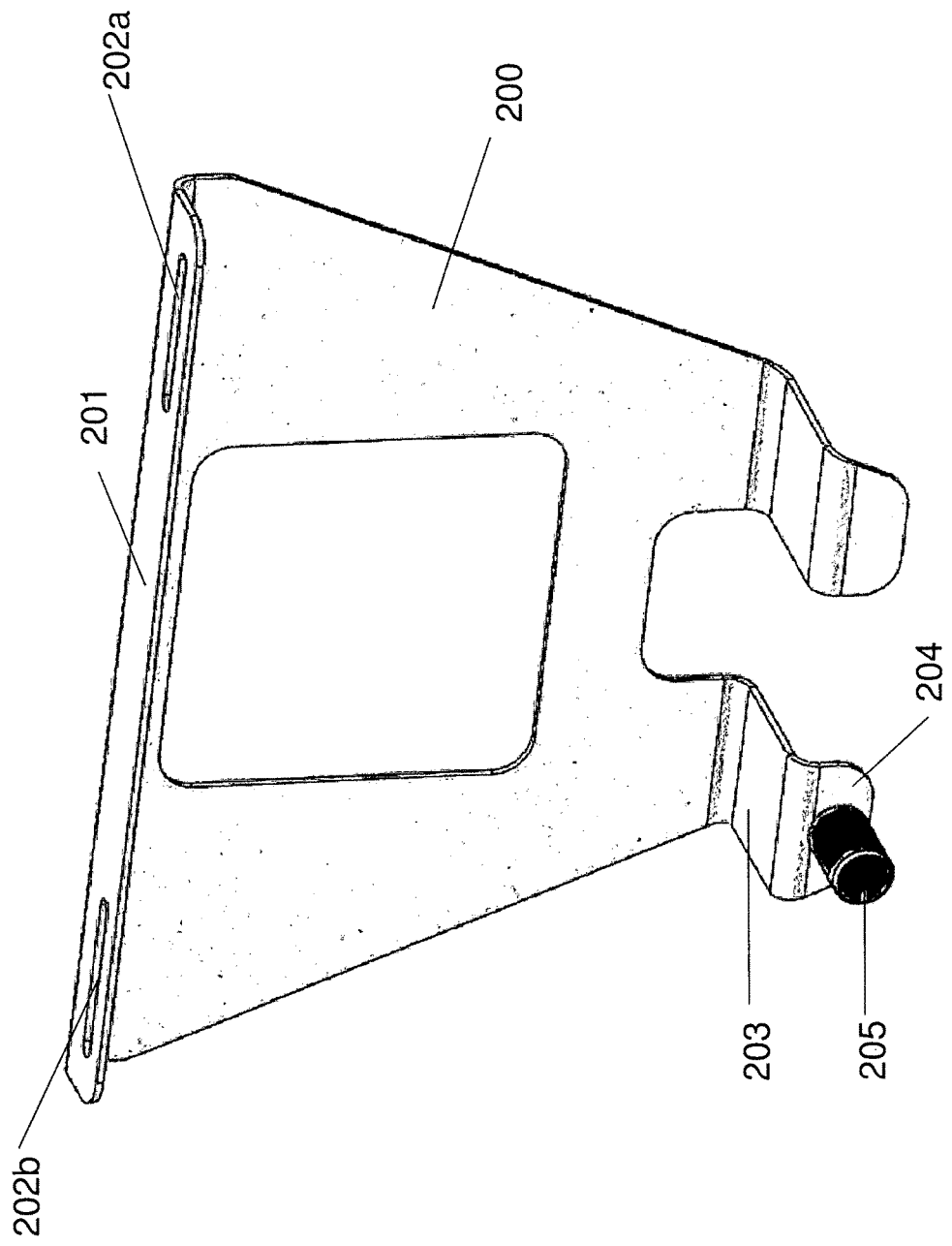
FIG. 12 is a diagram that shows an isometric view of exemplary detachable tilting device embodiment of FIG. 10.

FIG. 10 is a diagram that shows an exemplary detachable tilting device embodiment attached to a cephalometric platform according to the application. FIG. 12 is a diagram that shows an isometric view of the exemplary detachable tilting device embodiment of FIG. 10. As shown in FIG. 10, tilting unit or tilting means 200 can cause or determine a tilt of the collimator 10 and the collimator slit 11 relative to the active area 21 of the sensor 20 can include a thin metallic frame with an upper curved surface 201 provided with two notches 202a and 202b and at least one protrusion 203 with a curved extremity 204 (FIG. 12). A stop 205, for example made of plastic, can be integral or fixed to the surface of the curved extremity 204. According to one exemplary alignment method, the tilting means 200 can be fixed to a prescribed portion, edge or ridge of the cephalometric platform 200 for the purpose of aligning the collimator 10 in such a way that the stop 205 intersects the trajectory of the collimator 10 when the collimator 10 is translated by the actuation of the stepping motor 130.

Figure 13:
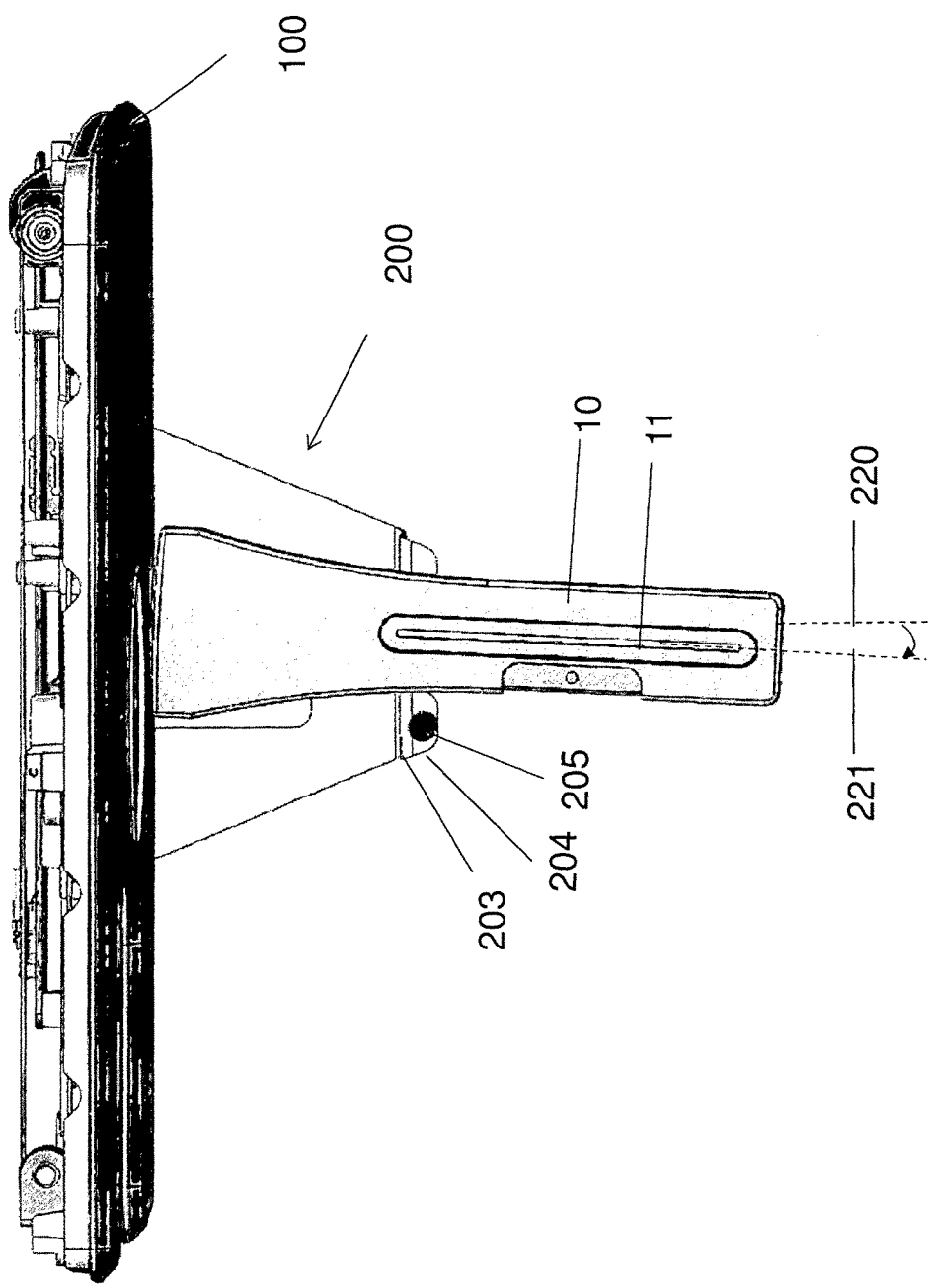
FIG. 13 is a diagram that shows a rear view of a secondary collimator and an exemplary detachable tilting device embodiment at a start position of the collimator sliding movement towards a rotation point or device according to the application.
Figure 14:
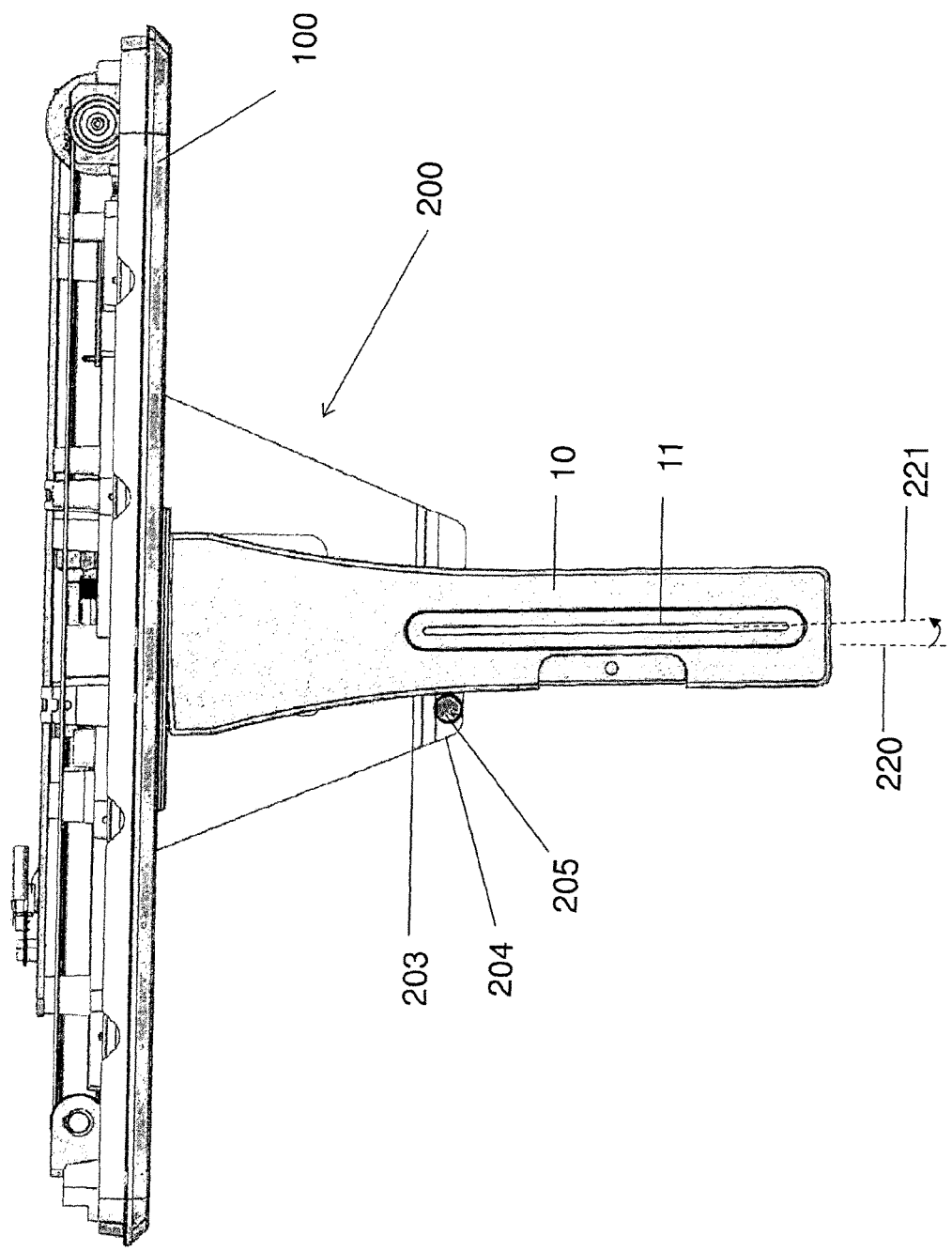
FIG. 14 is a diagram that shows a rear view of the secondary collimator and an exemplary detachable tilting device embodiment at the end position of the collimator in his sliding movement with a contact between the rotation device and the collimator according to the application.

FIG. 13 is a diagram that shows a rear view of a secondary collimator and an exemplary detachable tilting device embodiment at a start position of the collimator sliding movement towards a rotation point or device according to the application. FIG. 14 is a diagram that shows a rear view of the secondary collimator and an exemplary detachable tilting device embodiment at the end position of the collimator in his sliding movement with a contact between the rotation device and the collimator according to the application.

In certain alignment methods and/or apparatus embodiments according to the application, the collimator 10 is translated from a first position away from the stop 205 having a tilt in a first orientation, that is with the direction of the slit 11 of the collimator 10 forming a positive angle with the vertical direction 220 (see FIG. 13). During this translation of the collimator 10 (e.g., in the direction toward the stop 25), the fixing means 72a, 72b, 82a and 82b is not tightly fixed, the faces 54 and 64 are in contact. It must be reminded that the vertical direction 220 is also the direction of the active area 21 of the sensor 20. This initial tilt is created by the action of the spring 53 that tilts the platen 60 and the collimator 10 relative to the carriage 50 (see FIG. 6). First, the collimator 10 is translated towards the stop 205. Second, the edge of the collimator 10 contacts the stop 25, and a torque is applied on the collimator 10 and hence on the platen 60 that opposes the action of the spring 53. The tilt of the slit 11 of the collimator 10 relative to the vertical direction 220 (or the sensor direction, which can be horizontal or another prescribed orientation) progressively decreases as the collimator 10 continues to be progressively translated in the direction towards the stop 205. The tilt or angle of the slit 11 of the collimator 10 reaches the zero value and then becomes negative when the collimator 10 keeps on being translated (see FIG. 14).

Figure 15C:
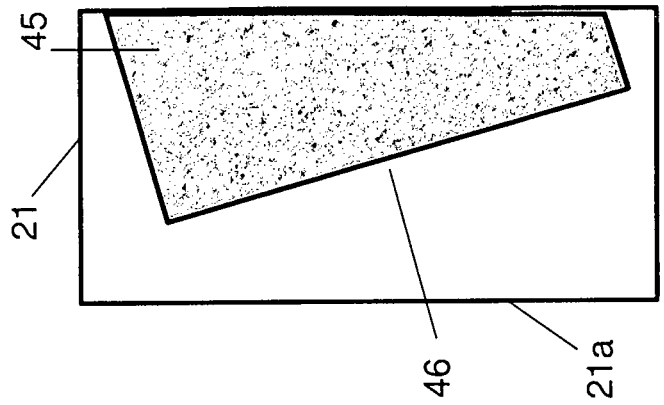
FIGS. 15a, 15b and 15c are diagrams that show exemplary projection images obtained by the cephalometric sensor when the x-ray beam is shaped by the secondary collimator when the secondary collimator is tilted on one side relative to the cephalometric sensor, when the secondary collimator is in good alignment with the cephalometric sensor and when the secondary collimator is tilted on the other side relative to the cephalometric sensor according to embodiments of the application.
Figure 15B:
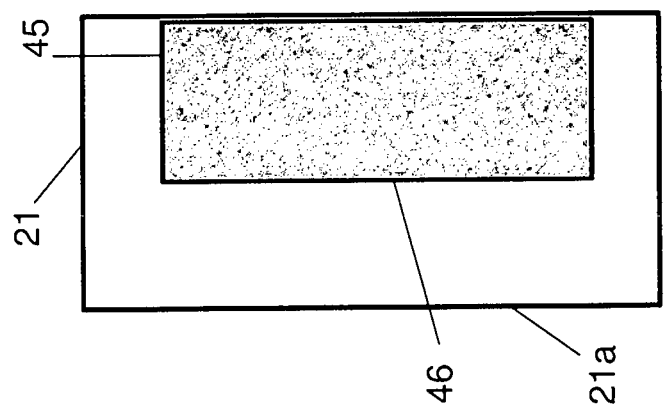
Figure 15A:
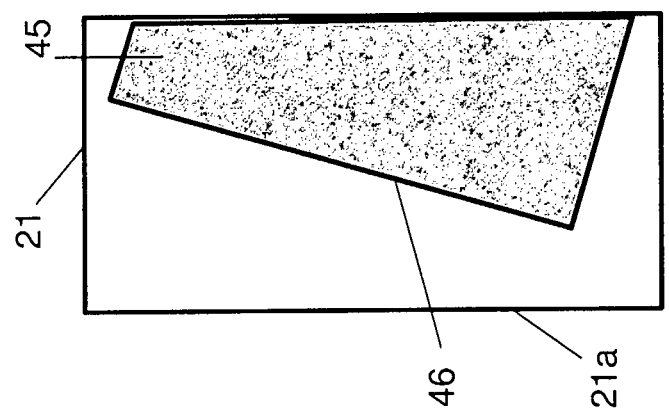

Meanwhile, during the translation of the collimator 10, the x-ray source emits an x-ray beam and blank images (e.g., projection images) can be captured at each position (e.g., step of the stepping motor) of the collimator 10. The area 45 of the surface of the active area 21 of the sensor 20 that is impinged by the x-ray beam 44 that passes through the tilted collimation slit 11 can be stored at each position of the collimator 10 during translation. In particular, each image (FIGS. 15a-15c) is associated to a known position of the collimator 10 (e.g., expressed in a number of steps carried out by the stepping motor 130). The surface 45 on the image can be characterized by an edge 46 that forms an angle with the edge 21a of the active surface 21 of the sensor 20. It will be obvious for the man skilled in the art that this angle is correlated with the angle formed between the direction of the slit 11 of the collimator 10 and the vertical direction 200, which is the same as the direction of the active surface area 21 of the sensor 20.

In certain exemplary embodiments, an initial tilt of the collimation slit 11 can be −10° relative to vertical and a final tilt of the collimation slit 11 can be +10° relative to vertical and at least 20 exposures can be obtained over the 20° range from the initial to final position so that at least 0.5° increments in tilt can be evaluated. Alternatively, the range from the initial to final position can be 10°, 15° or 30°. Further, in some embodiments, exemplary increments in tilt can be between 0.25° to 1°. In addition, the number of exposures during translation can be a few as 5-7 exposures or up to 40 or more exposures.

In one exemplary embodiment, the desired or best alignment of the collimator 10 and sensor 20 among the plurality of positions (e.g., projection images or frame) during translation can be determined. For example, an algorithm can automatically calculate the angle of the left and right edges of the irradiated surface on each frame. This edge can correspond to the sensor border 21a or to the edge 46 of the impinged surface. The angles absolute values can be summed to retrieve the image with the minimum angle value, that is the closest value to zero (see FIG. 15b). This image corresponds to a selected alignment of or the best alignment of the collimator 10 and sensor 20. In an embodiment using the stepping motor, the collimator 10 can be repositioned at this precise position that corresponds to the selected or correct alignment of the slit 11 of the collimator 10 with the active elongated area 21 of the sensor 20, with the collimator 10 being still submitted to the torque created by the contact with the stop 25. Then, the position of the collimator 10 can be fixed at the selected or correct alignment of the slit 11. Alternatively, the collimator 10 can be continuously translated or horizontally moved while pulsed or a series of short exposures are performed by the x-ray source 3, images captured by the sensor 10 and the position of the collimator 10 is recorded or detected at each exposure. For example, in one embodiment, a position of the collimator 10 during translation can be remotely sensed (e.g., emitters on the collimator 10 and sensors on the extra-oral imaging device 1, remote cameras or the like).

In one embodiment, to fix the angular position of the collimator 10, it is then necessary to screw tightly the screws 72a and 72b (see FIG. 5) so that the friction between the washers 82a and 82b on the surface of the platen surrounding the oblong holes 62a and 62b counterbalances the force exerted by the spring 53 on the platen. Then, the tilting means 200, which is preferably used only during the exemplary alignment processes, can be removed from the edge of the platform 100.

Figure 16:
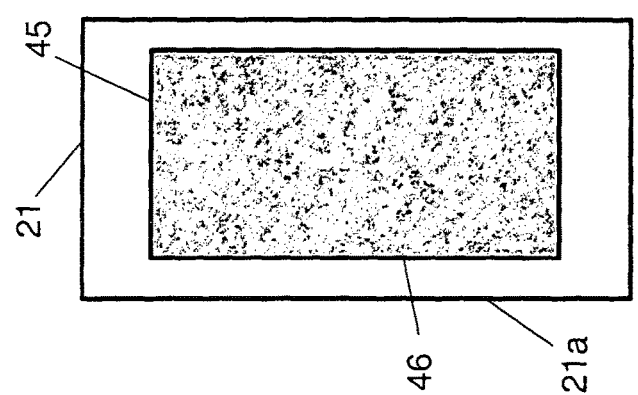
FIG. 16 is a diagram that shows an exemplary image obtained when the x-ray beam is aligned and centered relative to the cephalometric sensor according to embodiments of the application.

Once the tilt alignment is achieved, an additional or last step includes aligning the center of the slit 11 of the collimator 10 with the center of the active surface area 21 of the sensor 20 according to methods and/or apparatus known from the related art. Alternatively, the aligning the center of the slit 11 of the collimator 10 with the center of the active surface area 21 of the sensor 21 according to methods known from the related art can be performed before the exemplary tilt alignment embodiments according to the application described herein. Then, the image 45 is centered and aligned on the active surface 21 on the sensor 20 as shown in FIG. 16.

In certain exemplary embodiments, the stop 205 can be above the aperture 11 of the collimator 10. Alternative embodiments place the stop 205 near the middle of the aperture 11 of the collimator 10. In one exemplary embodiment, the stop 205 can be near the bottom or below the aperture 11 of the collimator 10, which can provide increased granularity or smaller sized increments of tilt during translation of the collimator 10 during alignment.

Consistent with exemplary embodiments of the present application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known. It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art. In the description herein, exemplary embodiments of the application can be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

As described herein, portions of some exemplary embodiments have been connected or joined together using screws. However, the application is not intended to be so limited as various example of fasteners can be used such as but not intended to be limited to mechanical fasteners like anchors, bolts, hardware, nails, nuts, pins, clips, rivets, rods, sockets, clamps, hangers, but also non-mechanical fasteners like adhesives or welds or permanent fasteners. Similarly, exemplary embodiments describe fixing means to couple an exemplary carriage to an exemplary platen. Exemplary fixing means herein can preferably provide a first engagement and a second engagement between the carriage 50 and platen 60. The first engagement by the fixing means between the carriage 50 and platen 60 can allow movement such as but not limited to rotation therebetween while an elastic or urging force can also be provided during the first engagement to set a prescribed rotation (e.g., 10° rotation therebetween) or prescribed position. The second engagement by the fixing means between the carriage 50 and platen 60 does not allow movement therebetween but sets a specific spatial or positional relationship therebetween and in some cases overcoming an elastic or urging force that can be maintained during the second engagement.

One conventional method to align the center of the slit 11 of the collimator 10 with the center of the active surface area 21 of the sensor 20 (e.g., sagittal plane of the skull must be parallel to the plane of the sensor at the time of the imaging and orthogonal to the median line of the x-ray beam) will now be described. When a cephalometric imaging apparatus is first installed in a dental site by a technician, it is necessary to adjust the position of the whole cephalometric imaging module, comprising the x-ray sensor and a patient holder, relative to the x-ray source, prior to any cephalometric imaging of patients. Conventionally, at least two radiopaque markers are located on the patient holder and a first x-ray control image of the patient holder (without any patient) is carried out. If the images of the at least two markers superimpose on the x-ray image, the cephalometric module is conveniently or correctly positioned relative to the x-ray source. On the contrary, if the images of the two markers do not superimpose, the cephalometric module is misaligned relative to the x-ray source and needs to be repositioned before capturing a second control image or additional control images. Note that the technician who installs the cephalometric imaging device does not know, at the time he changes the adjustment of the cephalometric module, whether the new adjustment is correct. Only subsequent control images taken after adjustment will give an assessment of the quality of the adjustment. Accordingly, the cephalometric installation requires an adjustment process including a repeated, back and forth method of (i) successive adjustments of the cephalometric module to the x-ray source and (ii) successive assessments by taking a follow-up control image.

The invention has been described in detail, and may have been described with particular reference to a suitable or presently preferred embodiment, but it will be understood that variations and modifications can be effected within the spirit and scope of the invention. For example, exemplary tilting unit embodiments can be reciprocally moved between a retracted position and an alignment position in contrast to being detachable. In addition, exemplary apparatus and/or method embodiments according to the application have been described relative to a combined cephalometric, panoramic and computed tomography dental imaging apparatus, but are intended to be applicable to stand-alone cephalometric imaging apparatus or cephalometric imaging apparatus with any additional mode(s) of operation or functionality. The presently disclosed exemplary embodiments are therefore considered in all respects to be illustrative and not restrictive.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. A method for aligning a cephalometric collimator to an extra-oral imaging system, the method comprising:
    mounting a cephalometric imaging unit to a base system, the system base adjustable in at least one direction and configured to support an x-ray source, the cephalometric imaging unit configured to mount a cephalometric sensor, the cephalometric imaging unit comprising a cephalometric patient positioning unit including a cephalometric collimator positioned between the x-ray source and the cephalometric sensor so that x-rays impinge the cephalometric sensor after passing through an elongated aperture of the cephalometric collimator;
    mounting a cephalometric alignment device to the cephalometric imaging unit; and
    obtaining a plurality of two-dimensional x-ray projection images of the cephalometric imaging unit while controllably moving the cephalometric collimator through a plurality of positions;
    selecting one of the plurality of two-dimensional x-ray projection images in accordance with a prescribed alignment characteristic; and
    aligning the cephalometric collimator to the extra-oral imaging system by fixing the cephalometric collimator in a position corresponding to the selected one of the plurality of two-dimensional x-ray projection images.

2. The method of claim 1, where the prescribed alignment characteristic includes relative alignment between and image of the vertical edge of the cephalometric collimator and a vertical edge of the cephalometric sensor.

3. The method of claim 1, further comprising aligning a center of the cephalometric collimator with a line connecting a focal spot of the x-ray beam and a center of the cephalometric sensor.

4. The method of claim 1, where the controllably moving the cephalometric collimator through the plurality of positions comprises rotating the cephalometric collimator through the plurality of positions.

5. The method of claim 4, where the rotating the cephalometric collimator through the plurality of positions comprises:
fixing the cephalometric collimator to a platen;
movably fixing the platen to a carriage; and
translating the carriage along a guide rail while the cephalometric collimator engages a stop.

6. The method of claim 5, where translating the carriage along a guide rail while the cephalometric collimator engages a stop comprises incrementally tilting the cephalometric collimator between an initial tilt position and a final tilt position with a range of 20° therebetween while the cephalometric collimator engages the stop.

7. The method of claim 5, where the stop engages the cephalometric collimator below an aperture of the cephalometric collimator.

8. The method of claim 1, where the cephalometric alignment device is detachably mounted to the cephalometric platform or the cephalometric patient positioning unit.

9. The method of claim 1, where the cephalometric patient positioning unit comprises
a forehead support; and
at least one temporal holding member, where the at least one temporal holding member is adjustable in at least one direction, where the at least one direction is a distance between two temporal holders; and where the forehead support is adjustable in at least two dimensions, the extra-oral imaging system further comprising:
a first mount mounted to the support base and configured to revolve the x-ray source and a first imaging sensor partially around a first imaging area; and
a first patient positioning unit coupled to the first mount and positioned between the x-ray source and the first imaging sensor so that x-rays impinge the first imaging sensor after radiating the first imaging area, where the first patient positioning unit comprises:
a patient positioning unit shield;
a chin support coupled to the first patient positioning unit shield and includes a chin positioning element; and
a forehead support coupled to the first patient positioning unit shield.

10. The extra-oral dental imaging system aligned by the method of claim 1.

* * * * *